United States Patent [19]

Lulai et al.

[11] Patent Number: 5,436,226
[45] Date of Patent: Jul. 25, 1995

[54] NATURAL SUPPRESSION OF SPROUTING IN STORED POTATOES USING JASMONATES

[75] Inventors: Edward C. Lulai; Paul H. Orr, both of East Grand Forks, Minn.; Martin T. Glynn, Grand Forks, N. Dak.

[73] Assignee: The United States of America, as represented by the Secretary of Agriculture, Washington, D.C.

[21] Appl. No.: 147,355

[22] Filed: Nov. 3, 1993

[51] Int. Cl.$^6$ .............. A01N 43/04; A01N 37/08; A23B 7/144; A23B 7/154

[52] U.S. Cl. .................. 504/291; 504/313; 504/320; 426/268; 426/321

[58] Field of Search .............. 504/313, 320, 291; 426/268, 321

[56] References Cited

U.S. PATENT DOCUMENTS 5,139,562  8/1992  Vaughn et al. ............ 71/88
5,198,254  3/1993  Nisperos-Carriedo et al. ..... 426/102
5,376,391 12/1994  Nisperos-Carriedo et al. ..... 426/102

FOREIGN PATENT DOCUMENTS 292220A  4/1990  Japan.
9118512 12/1991  WIPO.

OTHER PUBLICATIONS van den Berg, Jan H., et al., "Jasmonates and Their Role in Plant Growth and Development, with Special Reference to the Control of Potato Tuberization: A Review", *American Potato Journal*, vol. 68, #11, Nov. 1991, pp. 781–794.

Koda, Y., et al., Cab Abstracts, 1420674, 0Q046-02943, "Potato tuber-inducing activities of salicylic acid and related compounds", Abstract of *Journal of Plant Growth Regulation*, 1992, 11(4):215–219.

Ravnikar, M., et al., Cat Abstracts, 1341982, 0Q045-079064; 7Q018-04304, "Stimulatory effects of jasmonic acid on potato stem node and protoplast culture", Abstract of *Journal of Plant Growth Regulation*, 1992, 11(1):29–33.

Pelacho, A. M., and Mingo-Castel, A. M., Cab Abstracts, 1272312, 0Q045-03896; 7Q018-02031; 7K017-000739; 7W018-01733, "Jasmonic acid induces tuberization of potato stolons cultured in vitro", Abstract of *Plant Pathology*, 1991, 97(3):1253–1255.

Koda, Y., and Kikuta, Y., CAB Abstracts, 1230721, 0Q045-01105; 7Q018-00460; 7W018-01256, "Possible involvement of jasmonic acid in tuberization of yam plants", Abstract of *Plant and Cell Physiology*, 1991, 32(5): 629–633.

Ravnikar, M., and Gogala, N., CAB Abstracts, 1104410, 0Q044-02455, 7Q017-01254, 7K016-00594; 7W017-01327, "Regulation of potato meristem development by jasmonic acid in vitro", Abstract of *Journal of Plant Growth Regulation*, 1990, 9 (4): 233–236.

Hamburg, Mats and Gardner, Harold W., "Oxylipin pathway to jasmonates: biochemistry and biological significance", *Biochim. et Biophys. Acta.*, 1165(1), 1992, pp. 1–18.

Parthier, B., "Jasmonates, New Regulators of Plant Growth and Development: Many Facts and Few Hypotheses on their Actions", *Bot. Acta*, 104(1991),pp. 446–454.

(List continued on next page.)

Stress Factors in Leaf Senescence?", *J. Plant Growth Regul.*, 9:37–63, 1990.

*Primary Examiner*—G. Mark Clardy
*Attorney, Agent, or Firm*—M. Howard Silverstein; Randall E. Deck; John D. Fado

[57] ABSTRACT

A novel process is described for controlling sprouting in tubers and improving their processing qualities using naturally occurring compounds. Tuber sprouting and/or melanization which occurs during processing, such as cooking or frying, may be controlled by exposure of the tubers to an effective amount of a jasmonate. Further, by varying the amount of jasmonate applied to the tubers, either sprout inhibition or improvement of processed color quality or both, may be preferentially selected.

15 Claims, No Drawings

OTHER PUBLICATIONS

Koda, Yasunori and Okazawa, Yozo, "Detection of Potato Tuber-Inducing Activity in Potato Leaves and Old Tubers", *Plant Cell Physiol.*, 29(6):969-974, 1988.

Matsauki, Tomoko, et al., "The Influences of Jasmonic Acid Methyl Ester on Microtubules in Potato Cells and Formation of Potato Tubers", *Biosci. Biotech. Biochem.* 56(8), 1329-1330, 1992.

Yoshihara, Teruhiko, et al., "Structure of a Tuber-Inducing Stimulus from Potato Leaves" (*Solanum tuberosum L.*) *Argic. Biol. Chem.*, 53(10), 2835-2837, 1989, Yamane, Hisakazu, et al., "Syntheses of Jasmonic Acid Related Compounds and Their Structure-Activity Relationships on the Growth of Rice Seedings", *Agric, Biol. Chem.*, 44(12), 2857-2864, 1980.

Farmer, Edward E., and Ryan, Clarence A., "Interplant communication: Airborne methyl jasmonate induces synthesis of proteinase inhibitors in plant leaves", *Proc. Natl. Acad. Sci. USA,* vol. 87, pp. 7713-7716, Oct. 1990, Botany.

Abe, M., et al., "Cell cycle-dependent disruption of microtubules by methyl jasmonate in tobacco BY-2 cells", *Protoplasma,* 156:1-8, 1990.

Parthier, Benno, "Jasmonates: Hormonal Regulators or

NATURAL SUPPRESSION OF SPROUTING IN STORED POTATOES USING JASMONATES

BACKGROUND OF THE INVENTION

1. Field of the Invention

The invention relates to a method for natural suppression of sprouting and improvement of internal processing quality of stored potatoes.

2. Description of the Prior Art

Typically, tubers are harvested, allowed to suberize (i.e., allow the "skin" or periderm layer to form over wound areas) at warm temperatures for about 10 days, then gradually cooled down to the storage temperature of about 10° C. For the first 1-2 months after harvest, the tubers remain dormant and exhibit little inclination to sprout. However, after this period the tubers must be chemically treated or refrigerated at very cold temperatures to prevent sprouting from occurring, such sprouting causes numerous deleterious effects to the tubers. These include a loss of fresh weight, the conversion of starch to sugars, and a decrease in the quality and appearance of tubers sold fresh. Sprouts and the surrounding tissue also contain elevated levels of toxic glycoalkaloids, which are not destroyed by cooking.

In addition to the problems encountered with sprouting, stored potatoes convert starch to reducing sugars as they age and as a result of cold temperatures and other stresses. The development of reducing sugars in the raw product is very undesirable because the sugars combine via aldol condensations with amino acids during processing to form dark melanoidin pigments. Even small accumulations of reducing sugars in the raw product result in unacceptably dark and unmarketable finished product. Currently, the only technology available to partially control the accumulation of reducing sugars in stored potatoes is to store them at intermediate temperatures (approximately 9° or 10° C.), to minimize cold stress, and then slowly warm them before marketing to hopefully respire surplus sugars before processing. This procedure is not always successful and it precludes storage at cold temperatures which could otherwise be employed to inhibit disease and weight loss. Presently there is no effective means to biologically control or reduce the level of reducing sugars in potatoes. The inability to control or dissipate accumulation of reducing sugars in potatoes results in over 40 million dollars in losses each year and impedes the ability to develop new markets.

Chlorpropham (CIPC; 1-methylethyl-3-chlorophenylcarbamate) is currently used to control tuber sprouting throughout the industry. Although CIPC has been used effectively, it has been on the market for over three decades and no replacements or improvements to the technology of sprout control have been made commercially available during this time. In the U.S. and around the world, there is increasing emphasis on replacing synthetic control agents (agricultural chemicals) with natural biological control mechanisms that are safe and more environmentally acceptable.

For many centuries, the Incas of South America and their descendants have buried potato tubers in pits that are layered with soil and the leaves of Muna plants that belong to the mint family Lamiaceae, and the genera Minthostachys and Satureja. This treatment prevents sprouting and excessive fresh weight loss, and repels insect pests. These Muna plants contain copious amounts of essential oils that are substantially comprised of monoterpenes. Aliaga and Feldheim [*Ernahrung*, 9:254-256 (1985)] and Feldheim ["Practicability and Mode of Action of Quality Storage of Potatoes After Harvest," In Report of a Lecture Given to the German Institute for Quality Research (Plant Nutrition Products), March 1985, 6 pages] reported that the oil from the Muna plants was more effective than CIPC in inhibiting sprouting, fresh weight loss, and the incidence of rotted tuber parts over a period of 120 days. The authors also reported that the main components of the oil, including the monoterpenes α- and β-pinene and limonene, and the oxygenated monoterpenes pulegone and menthone/isomenthone, are effective in this regard.

Currently, several research groups in the United States and Europe are investigating alternative synthetic chemical inhibitors to tuber sprouting [Rama and Narasimham, J. Food Sci. Technol., 24:40-42 (1987)].

Vaughn et al. (U.S. Pat. No. 5,139,562) and Vaughn and Spencer (U.S. Pat. No. 5,129,951) disclosed that the oxygenated monoterpenes cineole, fenchone and menthol, as well as several aromatic aldehydes and alcohols, including thymol, hydrocinnamaldehyde, cuminaldehyde, salicylaldehyde, cinnamaldehyde, and benzaldehyde, may be advantageously used to inhibit tuber sprouting, fresh weight loss, rotting, and fungal growth.

Jasmonates are cyclopentanone compounds which are commonly present throughout the plant kingdom. The structures and bioactivities of jasmonates are thoroughly reviewed by Hamberg and Gardner (1992, Biochimica et Biophysica Acta, 1165:1-18) and Parthier (1991, Bot. Acta, 104:446-454), the contents of each of which are incorporated by reference herein. The structure of the free acid, jasmonic acid (JA), is as follows:

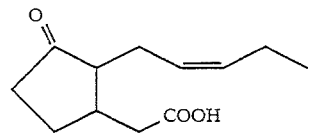

Jasmonates have been described as exerting a wide range of differing effects on virtually all plants, ranging from inhibition to promotion of plant processes. As described by Parthier, the effect exhibited on the plant may even be concentration dependent, with some processes stimulated at lower concentrations but inhibited at higher concentrations. A few examples of activities influenced by jasmonates include inhibition of seed germination and seedling growth, stimulation of seed germination (at lower concentrations), promotion of seed dormancy breaking, and promotion of leaf senescence. Ryan and Farmer (International patent application WO 91/18512, published Dec. 12, 1991) disclosed treating plants with jasmonates to induce production of defense proteins. Treatment of tomatoes, tobacco, alfalfa and transgenic tobacco plants was specifically disclosed. Tazaki (Japanese kokai 2-92220 (A), published Apr. 3, 1990, patent application no. 63-242432, filed Sep. 29, 1988), Yoshihara et al. (1989, Agric. Biol. Chem., 53:2835-2837), Matsuki et al. (1992, Biosci. Biotech. Biochem., 56:1329-1330), and Koda and Okazawa (1988, Plant Cell Physiol., 29:969-974) all disclosed treating potato stem fragments with jasmonates in culture to induce tuber formation.

SUMMARY OF THE INVENTION

We have now discovered a novel process for controlling sprouting in tubers and improving their processing qualities using naturally occurring compounds. Tuber sprouting may be inhibited and/or melanization which occurs during processing may be reduced by exposure of the tubers to an effective amount of jasmonate. With respect to the latter, treatment of tubers with jasmonate minimizes or controls the accumulation of reducing sugars, and hence reduces the development of undesirable dark pigments (melanization) which occurs during processing, such as during frying or cooking. Further, by varying the amount of jasmonate applied to the tubers, either sprout inhibition or reduction of melanization (improvement of processed color quality) or both, may be preferentially selected. We have unexpectedly found that exposure to low amounts of jasmonate provides greater sprout control but decreased improvement of processed color quality, while high amounts provide greater improvement in the processed color quality at the expense of poorer sprout inhibition. Exposure to intermediate amounts of jasmonate provides both tuber sprout control and processed color quality improvement.

In accordance with this discovery, it is an object of this invention to provide an improved method for suppression of tuber sprouting without necrosis or softening of the tuber. It is a further object to provide a method for inhibiting the sprouting of tubers under storage and going to fresh market using jasmonates and jasmonate related compounds applied as liquids, volatiles and fogs.

Another object of this invention is to provide a method for treating tubers that results in improved processing quality via improved processed product color, thereby improving marketability and reducing losses due to substandard processing quality.

Yet another object of this invention is to provide a method for suppression of tuber sprouting and improving processed product color using naturally-occurring compounds which have low mammalian toxicity, are rapidly biodegraded, do not impart an unpleasant taste or odor to the treated tubers, and which do not impart disease susceptibility.

Other objects and advantages of the invention will become readily apparent from the ensuing description.

DETAILED DESCRIPTION OF THE INVENTION

The commercial importance of inhibiting sprouting and weight loss of tubers is well known. A need exists for an effective method to inhibit or suppress tuber sprouting which uses a compound that is environmentally acceptable, has low mammalian toxicity, and that does not result in necrosis or softening of the tubers, or impart an unpleasant taste or odor thereto. Equally important, the sprout suppression method must not stress the potatoes and thereby cause negative effects on internal processing quality of the tubers; especially important in this regard, the method must not cause the potatoes to respond with increased sugar levels or cause the processed product to darken in color and become unacceptable for marketing.

According to this invention, there is provided a method for inhibiting sprouting of tubers and maintaining or improving their processing quality by exposing the tubers to a jasmonate or a jasmonate related compound. Although treatment with jasmonates is preferred, other jasmonate related compounds or jasmonate precursers, such as jasmone and phytodienoate may also be used. The jasmonates may be applied singly or in mixtures, in pure or substantially pure form, or optionally in a composition.

The term jasmonate is defined herein as jasmonic acid (JA), its isomers, and derivatives thereof which have: 1) a keto or hydroxy (free hydroxy or ester) moiety at the $C_6$ carbon, 2) a lower acyl side chain at $C_3$ (free acid or ester or conjugate), and 3) an n-pentenyl or n-pentyl side chain at $C_7$. A variety of jasmonates may be utilized herein, and include but are not limited to jasmonates of the formula:

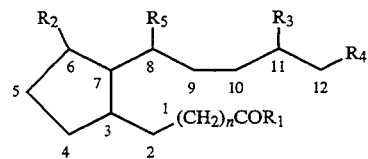

wherein n is 0, 1 or 2, $R_1$ is —OH, alkoxy, O-glucosyl or imino, $R_2$ is —OH, =O, alkoxy or O-glucosyl, and $R_3$, $R_4$ and $R_5$ are H, —OH, alkoxy or O-glucosyl, and/or wherein $R_1$ and $R_2$ or $R_1$ and $R_4$ together form a lactone, and further wherein the bonds between $C_3:C_7$, $C_4:C_5$ and $C_9:C_{10}$ may be double or single bonds. Preferred jasmonates include jasmonic acid (JA) [either the (—)- or (+)-7-iso- forms], 9,10-dihydro-JA, 4,5-didehydro-7-iso-JA, 3,7-didehydro-JA, cucurbic acid (CA), 6-epi-CA, 6-epi-CA-lactone, 12-hydroxy-JA, 12-hydroxy-JA-lactone, 11-hydroxy-JA, 8-hydroxy-JA, homo-JA, dihomo-JA, 11-hydroxy-dihomo-JA, 8-hydroxy-dihomo-JA, tuberonic acid (TA), TA-O-β-glucopyranoside, CA-O-β-glucopyranoside, amino acid conjugates of JA, as well as the corresponding lower alkyl esters of each of these acids. Particularly preferred jasmonates include jasmonic acid [(—)-JA or (+)-7-iso-JA or both], methyl jasmonate and 9,10-dihydrojasmonic acid and its lower alkyl ester.

Suitable compositions of the jasmonates of the invention may be prepared or may be naturally occurring. Naturally occurring compositions include but are not limited to oils such as oil from jasmine flowers or a wide variety of plant extracts (Hamberg and Gardner, ibid). The jasmonates may also be formulated with an inert carrier or solvent such as water, oils or alcohols. While as a practical matter, it is expected that pure or substantially pure jasmonate (or a mixture of jasmonates) will be formulated with a carrier, impure jasmonate or an above-mentioned oil or extract may also be formulated with a carrier. The practitioner skilled in the art will recognize that the jasmonate composition may be further formulated with, for example, emulsifying agents, fungicides or insecticides, or even with other sprout inhibitors. It is significant to note that when other agents are used for sprout control, the addition of jasmonate is particularly advantageous for improving the processing color quality, which is typically negatively affected after treatment with many other known sprout inhibitors. Examples of other sprout inhibitors which may be used herewith include, but are not limited to, the above-mentioned CIPC, the aromatic alcohols or aldehydes, or monoterpenes of Vaughn (U.S. Pat. Nos. 5,129,951 and 5,139,562), carvone or naphthalenes such as dimethyl naphthalene (Lewis and Kleinkoph, 1993, Potato Grower of Idaho, 22(7):20–21) the contents of each which are incorporated by reference herein.

The process of the invention is effective for the inhibition of sprouting and/or reduction of melanization during processing of a variety of tubers including but not limited to potatoes.

Preferred methods of exposure of the tubers to the jasmonates or related compounds involve exposure to the subject compounds while in a gas or vapor phase. These methods take advantage of the relatively high volatility of these compounds, and enjoy the benefit of ease of application over a large volume of tubers. In this embodiment, exposure of the tubers to the jasmonates may be achieved by providing the compounds in liquid or solid form and allowing or causing the same to volatilize into the atmosphere adjacent to or surrounding the tubers. Without being limited thereto, especially favored techniques for enhancing this volatilization include fogging or fuming such as by heating or sonicating a composition of jasmonate in carrier. Alternatively, the jasmonates may be volatilized by simply passing air or some other inert gas over the compounds. Rather than initially providing the jasmonates in liquid or solid form, they may also be provided as a gas directly admitted into the atmosphere adjacent the tubers.

Alternatively, the jasmonates or related compounds may be applied directly onto the tubers while in liquid form, such as by dipping or spraying with a solution or emulsion thereof. For example, spraying the tubers with an emulsion of the jasmonates as the tubers are passed along a conveyor into holding bins or storage areas would provide a convenient mode of application. The practitioner skilled in the art will recognize that suitable formulations of the jasmonates may optionally include a variety of well known solvents or suspending agents, including, but not limited to water. It is also understood that emulsifying agents may also be included.

In yet another alternative, the compounds may be incorporated into a slow release vehicle or carrier, such as by encapsulation or placement in a closed permeable container conventional in the art, to provide a controlled rate of release of the volatiles into the atmosphere over an extended period of time.

Exposure of the tubers to the jasmonates may be initiated at any time after harvest or during the storage of the tubers, such as prior to storage, or prior to dormancy breaking or sprouting. Surprisingly, unlike treatment with CIPC wherein the tubers must be allowed to suberize before they are exposed to the active agent, the tubers may be exposed to jasmonates immediately after harvest. This early treatment does not impair the wound healing abilities of the tubers. Exposure may be provided at a single occurrence, or alternatively continuously, or intermittently during storage.

In accordance with the preferred embodiment, for greatest improvement in processing quality, the tubers should be exposed to the compounds prior to stress (e.g. cold storage) or as early as possible thereafter. Such early exposure maximizes the processing quality of the tubers, minimizing the accumulation of reducing sugars and hence reducing or controlling the development of dark or brown products (melanization) during subsequent processing such as during frying. When storing the tubers in bins under storage conditions currently prevalent in the industry (about 9°–10° C.) or at colder temperatures, the tubers are preferably exposed to the jasmonates shortly after harvest, and exposure may be repeated as needed. While tubers previously held under storage conditions without treatment for long periods of time may also be treated for the purpose of effective sprout inhibition, the improvement in processing quality may be lessened. Fried products from such tubers may exhibit significantly darker coloration than tubers exposed to jasmonates at an early time.

The absolute amount of the jasmonates (or jasmonate related compounds) of the invention and their concentration in a vapor phase or liquid composition may vary and are selected to provide an effective inhibition of tuber sprouting and/or reduction of melanization during processing. An effective amount is defined herein as that quantity of jasmonate that: 1) significantly inhibits tuber sprouting in comparison with untreated tubers, and/or 2) significantly reduces or controls melanization of tubers during processing in comparison with untreated tubers. Suitable amounts and concentrations may be readily determined by the practitioner skilled in the art. The actual effective amount of the jasmonates may vary of exposure to the compound, the volume of tubers to be treated, environmental conditions such as temperature, humidity and air flow (affecting volatility and tuber metabolic activity), and the vehicle or carrier employed (affecting the release rate of the compounds into the atmosphere). As mentioned hereinabove, the amount may also vary in accordance with the desired result of the treatment, namely inhibition of tuber sprouting or reduction of melanization during processing. Exposure to relatively low amounts of jasmonate provides greater sprout control but decreased reduction of melanization during processing (less improvement of processed color quality), while relatively high amounts provide greater improvement in the processed color quality at the expense of poorer sprout inhibition. However, exposure to intermediate amounts of jasmonate provides both tuber sprout control and processed color quality improvement.

Without being limited thereto, the generally preferred concentration of the jasmonates for providing both inhibition of sprouting and reduction of melanization during processing is about 0.1 mM. Concentrations less than 0.1 mM, including but not limited to 0.001 mM and below, demonstrate increasing effectiveness as tuber sprout inhibitors, and it is envisioned that amounts as low as nanomole or picomole levels will also be effective. However, while sprout inhibition actually increases with decreasing concentration, the degree of improvement in processing color quality decreases concurrently. In contrast, concentrations of jasmonate greater than 0.1 mM, preferably greater than about 1 mM, exhibit increasing effectiveness for reducing melanization during processing (greater processing color quality), but decreasing sprout inhibition. When maximal color improvement is desired, high concentrations of jasmonate may be utilized in combination with other optional conventional sprout inhibitors.

The following examples are intended only to further illustrate the invention and are not intended to limit the scope of the invention which is defined by the claims.

EXAMPLE 1

Tubers were treated with various levels of jasmonates, or with CIPC, via a plurality of application methods to demonstrate the effectiveness of jasmonates as sprout inhibitors.

Potatoes (*Solanum tuberosum*, cv. Norchip) for these tests were grown at the Potato Research Farm, Grand Forks County, ND, under conventional practices. After harvest, about 90 potatoes without physical defects were selected for treatment in each test group. Tubers were exposed to test compounds by dipping, fogging or volatilization. For each application method, test groups were selected as follows: tubers exposed to one of three levels of methyl jasmonate (0.1 mM, 0.01 mM or 0.001 mM), tubers exposed to 1% CIPC (47 mM), and untreated tubers as a negative control. For all treatments except dipping, tubers were placed directly into 15 glass storage jars (Libby Glass Co., Toledo, Ohio) equipped with inlet and exhaust tubes, about 45–46 tubers per jar.

Dipping

Active agent was suspended in an aqueous solution using 0.25% triton X-100) at the appropriate concentration. Tubers were rolled in a shallow pan having a 0.6 cm depth of the test compound, allowed to drip dry, and placed into the above-mentioned storage jars. Jars were not ventilated for 24 hr.

Fogging

Tubers were placed into storage jars, whereupon the jars were sealed. The test compounds were formulated with a sunflower oil carrier at the approprite concentration, and fogs were generated using a propane fired fogging unit (Burgess, Chadwick, N.Y.). Fog was admitted into each treatment jar for 15 sec after which the jars were immediately capped. Jars were held without ventilation for ten hours.

Volatilizing

Again, tubers were placed directly into the storage jars and sealed. Test compounds at the appropriate concentrations were placed onto a folded filter paper acting as a wick and placed into a volatilizing chamber (a 120 ml glass container having a teflon lined screw top provided with inlet and outlet tubes). Ventilation air was passed through the volatilizing chamber, carrying the test compounds to the corresponding storage jars. This process was continued for 10 days.

Storage

All storage jars from each test group were placed in walk-in controlled environment rooms at 7°–10° C. to reflect full-scale potato storage environmental conditions. Jars were continuously ventilated with humidified fresh air (85–95% relative humidity) throughout the course of the experiment, the air in each jar being exchanged every 3–4 hours.

The tubers in each vessel were monitored for sprout growth every two days following jar filling, and the number of tubers having sprouts counted. The results are shown in Table 1, and show that jasmonates effectively suppress sprouting by all application methods at lower concentrations than CIPC.

EXAMPLE 2

Tubers were treated with jasmonates to demonstrate the effectiveness of jasmonates for reducing melanization during processing. Tubers were treated with methyl jasmonates or CIPC, stored, and examined for sprouting using the procedure described in Example 1. Once sprouting was observed, tubers were removed from the jar and processed into chips, fried, and evaluated for processed color quality by measurement of Agtron reflectance values of the fried chips. The results are shown in Table 2. Fried chips from jasmonate treated tubers exhibited reduced melanization in comparison to those treated with CIPC and untreated controls, demonstrating that jasmonates are effective for improving the processed product color.

It is understood that the foregoing detailed description is given merely by way of illustration and that modifications and variations may be made therein without departing from the spirit and scope of the invention.

TABLE I

Comparison of Jasmonate induced sprout suppression with untreated controls and the currently used commercial synthetic sprout inhibitor CIPC

| Treatment | Weeks Before Sprouting Occurred at Various Concentrations | | |
|---|---|---|---|
| VOLATIZED APPLICATION OF TREATMENTS | | | |
| untreated control samples | 6 | 6 | 6 |
| methyl jasmonate | 14 | 13 | 14 |
| | (0.1 mM) | (0.01 mM) | (0.001 mM) |
| chlorpropham (CIPC) | 15 | 15 | 15 |
| | (47 mM) | (47 mM) | (47 mM) |
| FOGGED APPLICATION OF TREATMENTS | | | |
| untreated control samples | 6 | 6 | 6 |
| methyl jasmonate | 12 | 12 | 12 |
| | (0.1 mM) | (0.01 mM) | (0.001 mM) |
| chlorpropham (CIPC) | 15 | 15 | 15 |
| | (47 mM) | (47 mM) | (47 mM) |
| DIPPED APPLICATION OF TREATMENTS | | | |
| untreated control samples | 6 | 6 | 6 |
| methyl jasmonate | 13 | 15 | 15 |
| | (0.1 mM) | (0.01 mM) | (0.001 mM) |
| chlorpropham (CIPC) | 15 | 15 | 15 |
| | (47 mM) | (47 mM) | (47 mM) |

TABLE II

Processed product color quality of untreated control tubers, jasmonate treated tubers and CIPC treated tubers. Agtron reflectance values (ranging from 0–100) indicate better processed product color quality with higher Agtron readings.
AGTRON READINGS FROM RESPECTIVE APPLICATION AND TREATMENT CONCENTRATIONS

| Treatment | Fogged | | | Dipped | | | Volatized | | |
|---|---|---|---|---|---|---|---|---|---|
| | H | M | L | H | M | L | H | M | L |
| untreated control | | 54 | | | 54 | | | 54 | |
| methyl jasmonate* | 66 | 62 | 57 | 60 | 59 | 57 | 55 | 57 | 58 |
| CIPC* | | 55 | | | 55 | | | 55 | |

*H, M and L indicate the following concentrations of methyl jasmonate treatment:
H = 0.1 mM
M = 0.01 mM
L = 0.001 mM
CIPC was applied per commercial labled instructions at 1% which is equivalent to 47 mM.

We claim:

1. A method for inhibiting sprouting and/or reduce darkening of tubers comprising the step of exposing tubers to a jasmonate compound in an amount effective to inhibit sprouting or reduce melanization during processing or both.

2. A method as described in claim 1 wherein said jasmonate is selected from the group consisting of (−)-jasmonic acid, (+)-7-iso-jasmonic acid, methyl jasmonate and 9,10-dihydro-jasmonic acid.

3. A method as described in claim 1 wherein said jasmonate is substantially pure.

4. A method as described in claim 1 wherein said jasmonate is in a composition with a carrier.

5. A method as described in claim 1 wherein said jasmonate is in a liquid phase and said step of exposing includes allowing said liquid to volatilize into the atmosphere adjacent said tubers.

6. A method as described in claim 1 wherein said step of exposing comprises contacting said tubers with said jasmonate in a liquid phase.

7. A method as described in claim 1 wherein said step of exposing comprises contacting said tubers with said jasmonate in a gas phase.

8. A method as described in claim 1 wherein said step of exposing comprises contacting said tubers with said jasmonate in a fog.

9. A method as described in claim 1 wherein said tubers are potatoes.

10. A method as described in claim 1 wherein said amount of jasmonate is effective to inhibit sprouting of said tubers.

11. A method as described in claim 1 wherein said amount of jasmonate is effective to reduce melanization of said tubers during processing.

12. A method as described in claim 11 further comprising exposing said tubers to a second sprout inhibiting agent.

13. A method as described in claim 12 wherein said second sprout inhibiting agent is selected from the group consisting of CIPC, aromatic alcohols, aromatic aldehydes, monoterpenes, carvone and naphthalenes.

14. A method as described in claim 1 wherein said amount of jasmonate is effective to both inhibit sprouting of said tubers and reduce melanization thereof during processing.

15. A method as described in claim 1 wherein said tubers are not coated with a composition comprising a polysaccharide polymer.

* * * * *